United States Patent [19]
Sembo

[11] Patent Number: 6,103,758
[45] Date of Patent: Aug. 15, 2000

[54] TICK CONTROLLING AGENT

[75] Inventor: Satoshi Sembo, Takarazuka, Japan

[73] Assignee: Sumitomo Chemical Company, Ltd., Osaka, Japan

[21] Appl. No.: 09/299,233

[22] Filed: Apr. 26, 1999

[30] Foreign Application Priority Data

Jul. 30, 1998 [JP] Japan ................................. 10-215512

[51] Int. Cl.⁷ ..................................................... A01N 43/08
[52] U.S. Cl. .............................................................. 514/471
[58] Field of Search ............................................. 514/471

[56] References Cited

U.S. PATENT DOCUMENTS

| | | | |
|---|---|---|---|
| 4,742,060 | 5/1988 | Shiokawa et al. | 514/252 |
| 4,849,432 | 7/1989 | Shiokawa et al. | 514/341 |
| 5,034,404 | 7/1991 | Uneme et al. | 514/365 |
| 5,304,566 | 4/1994 | Ishimitsu et al. | 514/357 |
| 5,532,365 | 7/1996 | Kodada et al. | 544/212 |
| 5,750,548 | 5/1998 | Friedel et al. | 514/357 |

FOREIGN PATENT DOCUMENTS

| | | |
|---|---|---|
| 2044595 | 11/1995 | Australia . |
| 0428941A1 | 5/1991 | European Pat. Off. . |
| 8217606 | 8/1996 | Japan . |

*Primary Examiner*—Allen J. Robinson
*Attorney, Agent, or Firm*—Birch, Stewart, Kolasch & Birch, LLP

[57] ABSTRACT

Tick controlling agent which comprises 1-(tetrahydrofuran-3-yl) methyl-3-methyl-2-nitroguanidine as an active ingredient has an excellent efficacy for controlling ticks. Applying an effective amount of 1-(tetrahydrofuran-3-yl)methyl-3-methyl-2-nitroguanidine to tick, host animal of tick or place where ticks inhabit is an excellent method for controlling ticks.

6 Claims, No Drawings

TICK CONTROLLING AGENT

FIELD OF THE INVENTION

The present invention relates to a tick controlling agent.

BACKGROUND OF THE INVENTION

Heretofore, as a controlling agent against ticks that maltreat domestic animals such as farm animals and pets, organophosphorus compounds or pyrethriod compounds have been known. In the field of pesticide, from the utilization of the same sort of agents for a long era, the decrease in the controlling efficacy is becoming a problem because of the resistance of the targeted pests. And the development of a new tick controlling agent is demanded.

SUMMARY OF THE INVENTION

The present invention serves a new tick controlling agent containing 1-(tetrahydrofuran-3-yl)methyl-3-methyl-2-nitroguanidine (hereinafter, referred as "the present compound") as an active ingredient, and a use of the present compound for controlling ticks.

DETAILED DESCRIPTION OF THE INVENTION

The present compound is known as an insecticidal and miticidal active ingredient in U.S. Pat. No. 5,532,365 and can be obtained according to the description in U.S. Pat. No. 5,532,365 or JP-Hei-10-67766A.

The examples of the ticks controlled by the tick controlling agents of the present invention include Haemaphysalis spp. such as *Haemaphysalis longicornis, Haemaphysalis japonica* and *Haemaphysalis flava*; Dermacentor spp. such as *Dermacentor recticulatus* and *Dermacentor taiwanensis*, Ixodes spp. such as *Ixodes ovatus* and *Ixodes persulcatus*, Boophilus spp. such as *Boophilus microplus*, and the like. They are ectoparasites of domestic animals such as farm animals (cattle, sheep, etc.) and pets (dogs, cats, etc.).

Further, the objective animals include Rodentia such as mice, rats, hamsters, squirrels and the like; Lagomorpha such as rabbits and the like; Carnivora such as ferrets and the like; Aves such as ducks, hens, pigeons and the like.

The tick controlling agents of the present invention are usually formulated with inert carrier such as solid carrier and liquid carrier.

The examples of formulations include liquid formulations such as emulsifiable concentrates, oil formulation, oily liquid formulation, aqueous liquid formulation, shampoo, suspensible concentrates and the like; dusts; wettable powder; granules; paste-type formulation; microencapsulated formulation; foaming formulation; aerosol formulation; liquid carbon dioxide solution; tablet; sheet formulation; resin formulation; injection formulation; capsule formulation; suppository formulation; and so on. The appropriate formulation is chosen when the present invention is employed.

Further, the amount of the present compound in the formulation depends on the sort of the formulation and usually from 0.005 to 50% by weight.

These formulations can be prepared, for example, by mixing the present compound with a solid carrier or liquid carrier, optionally added an auxiliary such as emulsifier, sticking agent and the like. The formulation may be molded if necessarily. The examples of the carriers and auxiliaries utilized for formulation are followings.

The examples of the solid carriers include natural or synthetic minerals such as clay, kaolin, talc, bentonite, sericite, quartz, sulfur, activated carbon, calcium carbonate, diatomaceous earth, pumice, calcite, sepiolite, white mica, silica, alumina, vermiculite, perlite and so on; small granules such as sawdust, corn spike, coconut shell, tobacco stem and so on; gelatin; vaseline; methylcellose; lanolin; lard; liquid paraffin; and so on. The examples of the liquid carriers include aromatic or aliphatic hydrocarbons such as xylene, toluene, alkylnaphthalene, phenylxylylethane, kerosene, gas oil, hexane, cyclohexane and so on; halogenated hydrocarbons such as chlorobenzene, dichlorobenzene, dichloroethane, trichloroethane and so on; alcohols such as methanol, ethanol, isopropyl alcohol, butanol, hexanol, ethylene glycol and so on; ethers such as diethyl ether, ethylene glycol dimethyl ether, diethylene glycol monomethyl ether, diethylene glycol monoethyl ether, propylene glycol monomethyl ether, tetrahydrofuran, dioxane and so on; esters such as ethyl acetate, butyl acetate and so on; ketones such as acetone, methyl ethyl ketone, methyl isobutyl ketone, cyclohexanone and so on; nitriles such as acetonitrile, isobutyronitrile and so on; sulfoxides such as dimethyl sulfoxide and so on; amides such as N,N-dimethylformamide, N,N-dimethylacetoamide and so on; vegetable oils such as soybean oil, cottonseed oil and so on; plant essential oil such as orange oil, hyssop oil, lemon oil and so on; water and so on. The examples of the propellants for foaming formulation and aerosol formulation include propane gas, butane gas, flon gas, liquefied petroleum gas, dimethyl ether, carbon dioxide and so on. The examples of the base materials for resin formulation include polyvinyl chloride, polyurethane and so on and optionally plasticizers such as phthalic acid esters (e.g. dimethyl phthalate, dioctyl phthalate), adipic acid esters and stearic acid may be added to these materials. The resin formulation can be prepared by mixing an active ingredient compound with the base material using usual mixer, and then molding by injection, thrusting, pressing and so on. It may be optionally derived to animal collar, ear tag for animals and so on via process of further molding and/or cutting.

The examples of auxiliaries for formulation include non-ionic surfactants such as polyoxyethylene fatty acid ester, polyoxyethylene fatty acid alcohol ether and so on; ionic emulsifiers such as alkylsulfate salt, alkylsulfate salt, arylsulfonate salt and so on; dispersing agents such as lignin-sulfonate salt, methylcellulose and so on; sticking agents such as carboxymethylcellose, gum arabic, polyvinyl alcohol, polyvinyl acetate and so on; coloring agents such as ferric oxide, titanium oxide, prussian blue, alizarin dye, azo dye, phthalocyanine dye and so on.

The present agents can be optionally include more active ingredient other than the present compound.

The examples of the active ingredient other than the present compound include pyrethroid compounds such as permethrin, phenothrin, allethrin, pyrethrin, cyphenothrin, cyfluthrin, fenvalerate, fenpropathrin, transfluthrin and so on; organophosphorus compounds such as dichlorvos, tetrachlorvinfos, fenthion, chlorpyrifos, diazinone and so on; carbamate compounds such as propoxur, carbaryl, metoxadiazone, fenobcarb and so on; chitin-synthesis inhibitors such as lufenuron, chlorfluazuron, hexaflumuron, cyromazin, 1-(2,6-difluorobenzoyl)-3-[2-fluoro-4-(1,1,2,3,3-hexafluoropropoxy)phenyl]urea and so on; juvenile hormone like compounds such as methoprene, hydroprene, fenoxycarb and so on; N-phenylpyrazole type compounds; endoparasites for animals such as milvemicin, abamectin, ivermectin and so on; pest repellents such as N,N-diethy-m-toluamide (Deet), limonene, linalool, citronellal, menthol, menthone, hinokitiol, geraniol, eucalyptol, indoxacarb, carane-3,4-diol and so on; synergists such as piperonyl butoxide, octachlorodipropyl ether, N-(2-ethylhexyl)bicyclo [2.2.1] hept-5-ene-2,3-dicarboximide, isobornyl thiocyanatoacetate, N-(2-ethylhexyl)-1-isopropyl-4-methylbicyclo [2.2.2] oct-5-ene-2,3-dicarboximide, and so on.

The present compound can be applied to a tick, a host animal of ticks or a place where ticks inhabit, usually as the above-mentioned formulation by the known methods. The application methods for host animals include endermism and non-endermism.

Examples of endermism include spot-on or pour-on application of oily or aqueous liquid formulation; application onto the body surface of animals using oil formulation, emulsion, shampoo, dusts, aqueous dilution of wettable powder, foaming formulation or aerosol formulation; and putting collar, ear-tag or the like of resin formulation on the neck or ear of animals. Spot-on treatment is an application method that is applying liquid formulation onto a skin between blade bones of an animal and pour-on treatment is an application method that is applying liquid formulation along a back of an animal.

Examples of non-endermism include peroral application, subcutaneous application, injection, implant and application on mucosa. The administration is by the form of tablet, resin formulation, capsule, liquid formulation, injection formulation and suppository formulation. In the present invention, endermism is preferred.

The present compound is also applied to a place where ticks inhabit, for examples, floors, outdoors and so on, by utilizing a formulation of dusts, granules, oil formulation, aerosol formulation and wettable powder.

The application amount of the present compound depends on the applied place. For example, the dosage applying to animals is usually 0.01 to 1000 mg/kg and the dosage applying to floor, outdoors or the like is usually 0.1 to 10000 mg/m$^2$.

EXAMPLES

Hereinafter, the present invention is explained by examples in detail.

Formulation Example 1

Ten parts by weight of the present compound and 90 parts by weight of ethanol are mixed to afford spot-on formulation or pour-on formulation.

Test Example 1

A designated amount of acetone solution containing the present compound was uniformly applied to the bottom of a glass petri dish (7 cm in diameter) and dried by air. Into the glass petri dish, about 10 to 20 infant ticks (*Haemaphysalis longicornis*) were deposited, the upper portion of the glass petri dish was covered by plastic film and the lethal ratio was examined 24 hours later. Each test was repeated thrice. The test results are given in table 1.

TABLE 1

| Test Example No. | Dosage of the present compound (mg/m$^2$) | Lethal Ratio (%) |
|---|---|---|
| 1-1 | 0.2 | 91.4 |
| 1-2 | 0.02 | 73.9 |

Test Example 2

About 30 to 50 infant ticks (*Haemaphysalis longicornis*) were deposited on the ears of a rabbit (Std: NZW, female, weight : 2.4 kg), the ears were covered by a cotton bag (5 cm×10 cm), and the bag was fastened by a sticking tape. After 2 days, the number of the infant ticks parasitic on the ears was counted and each 0.1 mL of a mixture solution of 10 parts of the present compound and 90 parts of diethylene glycol monoethyl ether was applied on each ear. The lethal ratio was examined 3 days after the application. The lethal ratio was 95%.

Reference Example 1

A designated amount of acetone solution containing the present compound was applied to filter paper. On the periphery of the filter paper, a tangle (sticking agent) was applied to keep mites from escaping. About 20 adult mites (*Dermatophagoides farinae* or *Tyrophagus putrescentiae*) were deposited onto the filter paper, forcefully exposed, and the lethal ratio was examined 24 hours later. Each test was repeated twice. The results are given in table 2.

TABLE 2

| Test Example No. | Dosage of the present compound (mg/m$^2$) | Tested mite | Lethal Ratio (%) |
|---|---|---|---|
| Ref. 1-1 | 800 | *D. farinae* | 2.2 |
| Ref. 1-2 | 800 | *T. putrescentiae* | 2.5 |

The present compound has an excellent tick-controlling activity as shown in table 1, though it has a low miticidal activity against house dust mites as shown in table 2.

Reference Example 2

Forty female adults of two-spotted spider mite (*Tetranychus urticae*) were placed on a planted kidney bean that were sown seven days earlier. After 1 day, 30 ml of an aqueous dilution of the wettable powder containing the present compound prescribed below was uniformly applied to the kidney bean on which the spider mites were placed. Eight days after application, the damage to the seedleaf and first leaf was examined. Kidney beans without the application of the agent was also examined as a comparison. The result are given in table 3.

| (Prescription of the wettable powder) | |
|---|---|
| The present compound | 0.05 |
| Sorpol 5039 (Toho Chemical Product) | 10.0 |
| Demol SNB (Kao Corp. Product) | 2.0 |
| Tokuseal GU-N (Tokuyama Soda Product) | 45.0 |
| Cerogen 7A (Daiichi Kogyo Product) | 1.0 |
| SP clay (Shokozan Product) | Balance |
| Total | 100.0 (parts by weight) |

TABLE 3

| Test Example No. | Applied Concentration of the present compound (ppm) | Degree of Damage [*1] |
|---|---|---|
| Ref. 2 | 500 | 100 |

[*1] Degree of Damage

100: The same damage as control.

0: No damage by two-spotted spider mites.

The present compound has an excellent tick-controlling activity as shown in table 1, though it has a low miticidal activity against spider mites that are harmful against plants as shown in table 3.

What is claimed is:

1. A method for controlling ticks which comprises applying an effective amount of 1-(tetra hydrofuran-3-yl)methyl-2-nitroguanidine to a tick, a host animal of ticks in need of treatment or an infested locus of ticks.

2. The method according to claim 1, wherein 1-(tetrahydrofuran-3-yl)methyl-2-nitroguanidine is applied to the host animal of ticks in need of treatment.

3. The method according to claim 2, wherein the dosage of 1-(tetrahydrofuran-3-yl)methyl-2-nitroguanidine is 0.01 to 10,000 mg of 1-(tetrathydrofuran-3-yl)methyl-2-nitroguanidine per 1 kg of said host animal of ticks in need of treatment.

4. The method according to claim 1, wherein 1-(tetrahydrofuran-3-yl)methyl-2-nitroguanidine is applied to the infested locus of ticks.

5. The method according to claim 4, wherein the dosage of 1-(tetrahydrofuran-3-yl)methyl-2-nitroguanidine is 0.1 to 10,000 mg of 1-(tetrahydrofuran-3-yl)methyl-2-nitroguanidine per 1 $m^2$ of the infested locus of ticks.

6. The method according to claim 2, wherein said tick is selected from the group consisting of Haemaphysalis spp., Dermacentor spp., Ixodes spp., and Boophilus spp.

* * * * *